(12) United States Patent
Papac et al.

(10) Patent No.: US 9,554,702 B2
(45) Date of Patent: Jan. 31, 2017

(54) MICROSCOPE-LESS WIDE FIELD-OF-VIEW SURGICAL OCT VISUALIZATION SYSTEM

(71) Applicant: NOVARTIS AG, Basel (CH)

(72) Inventors: Michael Papac, Lake Forest, CA (US);
Lingfeng Yu, Lake Forest, CA (US);
Tammo Heeren, Aliso Viejo, CA (US)

(73) Assignee: Novartis AG, Basel (CH)

( * ) Notice: Subject to any disclaimer, the term of this patent is extended or adjusted under 35 U.S.C. 154(b) by 105 days.

(21) Appl. No.: 14/576,306

(22) Filed: Dec. 19, 2014

(65) Prior Publication Data

US 2015/0173608 A1 Jun. 25, 2015

Related U.S. Application Data

(60) Provisional application No. 61/920,347, filed on Dec. 23, 2013.

(51) Int. Cl.
*A61B 3/12* (2006.01)
*A61B 3/10* (2006.01)
*G02B 27/14* (2006.01)
*G02B 21/00* (2006.01)

(52) U.S. Cl.
CPC ............ *A61B 3/102* (2013.01); *G02B 27/141* (2013.01); *G02B 21/0012* (2013.01)

(58) Field of Classification Search
CPC ........... A61B 3/102; A61B 3/14; A61B 3/125; A61B 3/13; A61B 1/06; A61B 2090/3735; A61B 34/20; A61B 3/12; G02B 1/043
USPC ........ 351/206, 246, 221, 208, 210; 606/4, 5; 356/479; 359/663, 201.2
See application file for complete search history.

(56) References Cited

U.S. PATENT DOCUMENTS

| | | |
|---|---|---|
| 8,403,921 B2 | 3/2013 | Palankar et al. |
| 2008/0212738 A1 | 9/2008 | Gertner et al. |
| 2009/0257065 A1 | 10/2009 | Hauger et al. |
| 2010/0324543 A1* | 12/2010 | Kurtz ............... A61F 9/008 606/6 |
| 2011/0202044 A1 | 8/2011 | Goldsheleger et al. |
| 2012/0092615 A1 | 4/2012 | Izatt et al. |
| 2012/0274900 A1 | 11/2012 | Horn et al. |
| 2013/0141695 A1 | 6/2013 | Buckland et al. |
| 2013/0194581 A1 | 8/2013 | Yoshida |
| 2013/0231644 A1 | 9/2013 | Hanft et al. |
| 2013/0235343 A1 | 9/2013 | Hee et al. |
| 2013/0278898 A1 | 10/2013 | Kato |

(Continued)

FOREIGN PATENT DOCUMENTS

| | | |
|---|---|---|
| EP | 2815694 A1 | 12/2014 |
| WO | WO 2012/166116 | 12/2012 |

OTHER PUBLICATIONS

International Search Report and Written Opinion issued for PCT/US2014/071153, dated Mar. 31, 2015, 11 pgs.

*Primary Examiner* — Hung Dang
(74) *Attorney, Agent, or Firm* — S. Brannon Latimer

(57) ABSTRACT

A surgical imaging system can comprise a light source, configured to generate an imaging light beam; a beam guidance system, configured to guide the imaging light beam from the light source; a beam scanner, configured to receive the imaging light from the beam guidance system, and to generate a scanned imaging light beam; a beam coupler, configured to redirect the scanned imaging light beam; and a wide field of view (WFOV) lens, configured to guide the redirected scanned imaging light beam into a target region of a procedure eye.

21 Claims, 7 Drawing Sheets

(56) References Cited

U.S. PATENT DOCUMENTS

2014/0107634 A1 4/2014 Vogler et al.
2014/0125952 A1 5/2014 Buckland et al.
2015/0230702 A1 8/2015 Uhlhorn et al.

* cited by examiner

MICROSCOPE-LESS WIDE FIELD-OF-VIEW SURGICAL OCT VISUALIZATION SYSTEM

PRIORITY INFORMATION

The present application claims the benefit of U.S. Provisional Patent Application No. 61/920,347, filed Dec. 23, 2013 the disclosure of which is incorporated by reference herein in its entirety.

BACKGROUND

Technical Field

Embodiments disclosed herein are related to improved visualization for vitreo-retinal, glaucoma, or other ophthalmic surgeries. More specifically, embodiments described herein relate to a microscope-less wide-field-of-view surgical optical coherence tomography (OCT) visualization system.

Related Art

Developing techniques to assist ophthalmic surgery with imaging and visualization is one of the hottest areas of development and innovation. One class of ophthalmic surgeries, the vitreo-retinal procedure, involves vitrectomy, the removal of the vitreous body from the posterior chamber to access the retina. The successful execution of vitrectomy requires an essentially complete removal of the vitreous, including the most challenging regions near the vitreous base. Using imaging techniques and devices can be of substantial help to improve the efficiency of the vitreous removal.

However, assisting vitrectomy with imaging is particularly challenging for several reasons. One of them is that the vitreous is transparent. Another challenge is that visualization of the periphery requires imaging beams with a high angle of obliqueness. Similar visualization issues exist during membrane peeling procedures. At present, typically microscope or video-microscope imaging is used to address the former challenge, and wide angle contact-based or non-contact based lenses are used to address the latter challenge, in each case with limited success.

Improvement of the imaging can be achieved by using optical coherence tomography (OCT), a technique that enables visualization of the target tissue in depth by focusing a laser beam onto the target, collecting the reflected beam, interfering the reflected beam with a reference beam and detecting the interference, and measuring the reflectance signature within the depth of focus of the beam. The result is a line scan in depth, a cross-sectional scan, or a volumetric scan.

OCT has become common practice in the clinic as a diagnostic tool. Surgeons take pre-op images into the operating room for reference. OCT scanning is currently not available in the operating room, and thus does not support decision making during surgery. Pre-op images have limited utility following morphologic modifications to the target during a procedure.

Efforts to develop real-time intra-surgical OCT systems are being made by multiple companies ranging from startups to large corporations. The approaches to intra-surgical OCT to date have been microscope-based or endoprobe-based. However, standard surgical microscopes are designed for visible wavelength and, therefore, may not provide satisfactory near-infrared (NIR) performance for OCT imaging. Accordingly, integrating OCT into standard surgical microscopes can require substantial modifications of the microscope. Further, these modifications can be microscope specific dependent on the particular features and optical elements of each microscope.

Accordingly, there is a need for improved devices, systems, and methods that facilitate real-time, intra-surgical, wide-field of view OCT imaging by addressing one or more of the needs discussed above.

SUMMARY

The presented solution fills an unmet medical need with a unique solution to provide wide-field of view OCT imaging intra-surgically, without surgical overhead or disruption to the surgical workflow, with a comparatively low entrance price, suitable for a consumable product.

Consistent with some embodiments, a surgical imaging system comprises: a light source, configured to generate an imaging light beam; a beam guidance system, configured to guide the imaging light beam from the light source; a beam scanner, configured to receive the imaging light from the beam guidance system, and to generate a scanned imaging light beam; a beam coupler, configured to redirect the scanned imaging light beam; and a wide field of view (WFOV) lens, configured to guide the redirected scanned imaging light beam into a target region of a procedure eye.

Consistent with some embodiments, an apparatus for use in a surgical imaging system, the apparatus comprises: a beam coupler, configured to redirect a scanned imaging light beam into an optical pathway of a surgical microscope; and a wide field of view (WFOV) lens, configured to guide the redirected scanned imaging light beam into a target region of a procedure eye. The beam coupler and the WFOV lens can be integrated, and the integrated beam coupler and WFOV lens can be a consumable product configured for use in a single surgical procedure. The apparatus can also include a beam scanner, configured to receive an imaging light from a beam guidance system, and generate the scanned imaging light beam. The beam coupler and the beam scanner can be integrated, and the integrated beam coupler and beam scanner can be a consumable product configured for use in a single surgical procedure.

Additional aspects, features, and advantages of the present disclosure will become apparent from the following detailed description.

Figure 1:
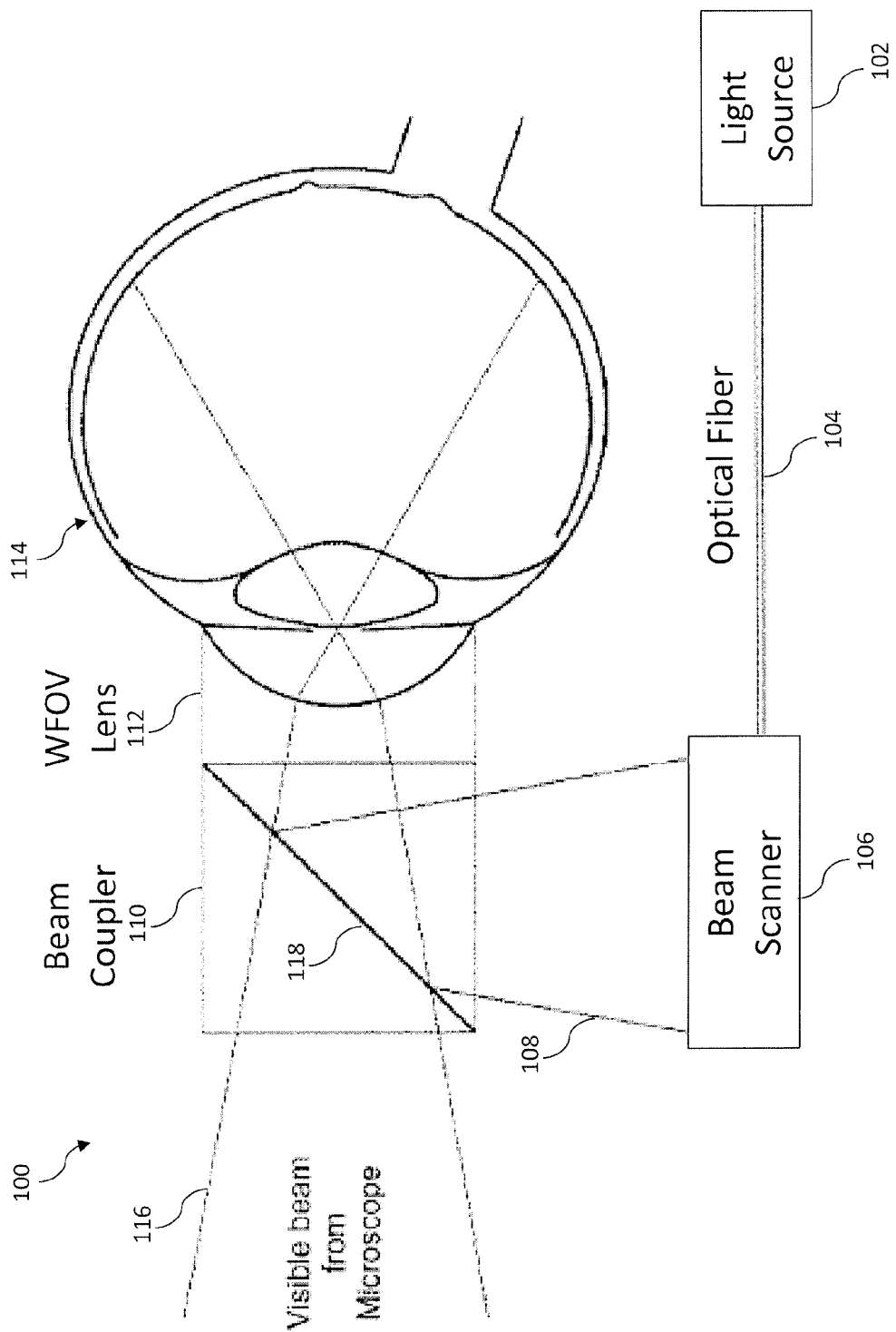
FIG. 1 is a diagram illustrating a microscope-less wide-field-of-view surgical OCT visualization system.

In the drawings, elements having the same designation have the same or similar functions.

DETAILED DESCRIPTION

In the following description specific details are set forth describing certain embodiments. It will be apparent, however, to one skilled in the art that the disclosed embodiments may be practiced without some or all of these specific details. The specific embodiments presented are meant to be illustrative, but not limiting. One skilled in the art may realize other material that, although not specifically described herein, is within the scope and spirit of this disclosure.

The real-time, intra-surgical, wide-field of view OCT imaging systems of the present disclosure provide numerous advantages relative to microscope-based OCT systems, including (1) reduced complexity of usage with a large number of different surgical microscopes; (2) reduced capital expense; (3) optical access to large variety of laser scanning visualization techniques; (4) consumable product and revenue source; and (5) wider scan angles, including the ability to scan in the periphery of the eye, by removing the constraints of delivering laser energy and collecting signal through the microscope optics. The real-time, intra-surgical, wide-field of view OCT imaging systems of the present disclosure also provide numerous advantages relative to endoprobe-based OCT systems, including (1) non-invasive OCT imaging; (2) simplified surgical workflow; (3) volume scan ability; (4) more stabilized OCT imaging with fewer motion related artifacts; (5) improved lateral resolution; and (6) the ability to be combined with surgical microscope imaging.

The surgical imaging system can be configured to facilitate delivery of intra-surgical wide angle laser scanning via a surgical lens of contact based or non-contact based. The laser scanning can be diagnostic and/or therapeutic in nature. Diagnostic laser scanning can include optical coherence tomography (OCT) imaging. For example, such a system may provide wide-field intra-surgical OCT without disrupting the surgical workflow. If non-visible laser wavelengths are used, then the contact lens can also serve as a standard surgical contact lens. A non-contact version of the surgical imaging system can be implemented in a manner similar to a binocular indirect ophthalmomicroscope (BIOM). Coupled with a real-time acquisition and display system the surgical imaging system can improve intra-surgical visualization. Further, the surgical imaging system can be operable independent of a microscope, and can even be used without a microscope. The surgical imaging system can also be coupled to a stereoscopic camera viewing system as a microscope replacement technology and/or a surgical guidance technology for surgical robots or remote surgical systems.

The surgical imaging system can be configured to image particular regions-of-interest with higher resolution, such as macula/fovea, optic disk, and/or trabecular meshwork/Schlemm's canal. To this end, the surgical imaging system can include a secondary lens system configured to provide independently adjustable magnification to the laser beam path, the microscope optical path, and/or a combined laser beam and microscope path.

FIG. 1 illustrates a surgical imaging system 100. The surgical imaging system 100 can include a light source 102 configured to generate an imaging light beam. The light source 102 can have an operating wavelength in the 0.2-1.8 micron range, the 0.7-1.4 micron range, and/or the 0.9-1.1 micron range. The surgical imaging system 100 can include a beam guidance system, including an optical fiber 104 and/or free space, configured to guide the imaging light beam from the light source.

The surgical imaging system 100 can also include a beam scanner 106 configured to receive the imaging light from the beam guidance system and generate a scanned imaging light beam 108. The beam scanner 106 can be configured to generate the scanned imaging light beam 108 having any desired one-dimensional or two-dimensional scan patterns, including a line, a spiral, a raster, a circular, a cross, a constant-radius asterisk, a multiple-radius asterisk, a multiply folded path, and/or other scan patterns. The beam scanner 106 can include one or more of a micro-mirror device, a MEMS based device, a deformable platform, a galvanometer-based scanner, a polygon scanner and/or a resonant PZT scanner. The beam scanner 106 can also include focusing optics for defining a depth of focus of the scanned imaging light beam 108. When present, the focusing optics of the beam scanner 106 can be fixed or adjustable. Adjustable focusing optics or zoom lenses within the beam scanner 106 can facilitate scanning of a region of interest with increased resolution and depth-of-field.

The surgical imaging system can also include a beam coupler 110 configured to redirect the scanned imaging light beam 108 towards a wide field of view (WFOV) lens 112 configured to guide the redirected scanned imaging light beam into a target region of a procedure eye 114.

Figure 2:
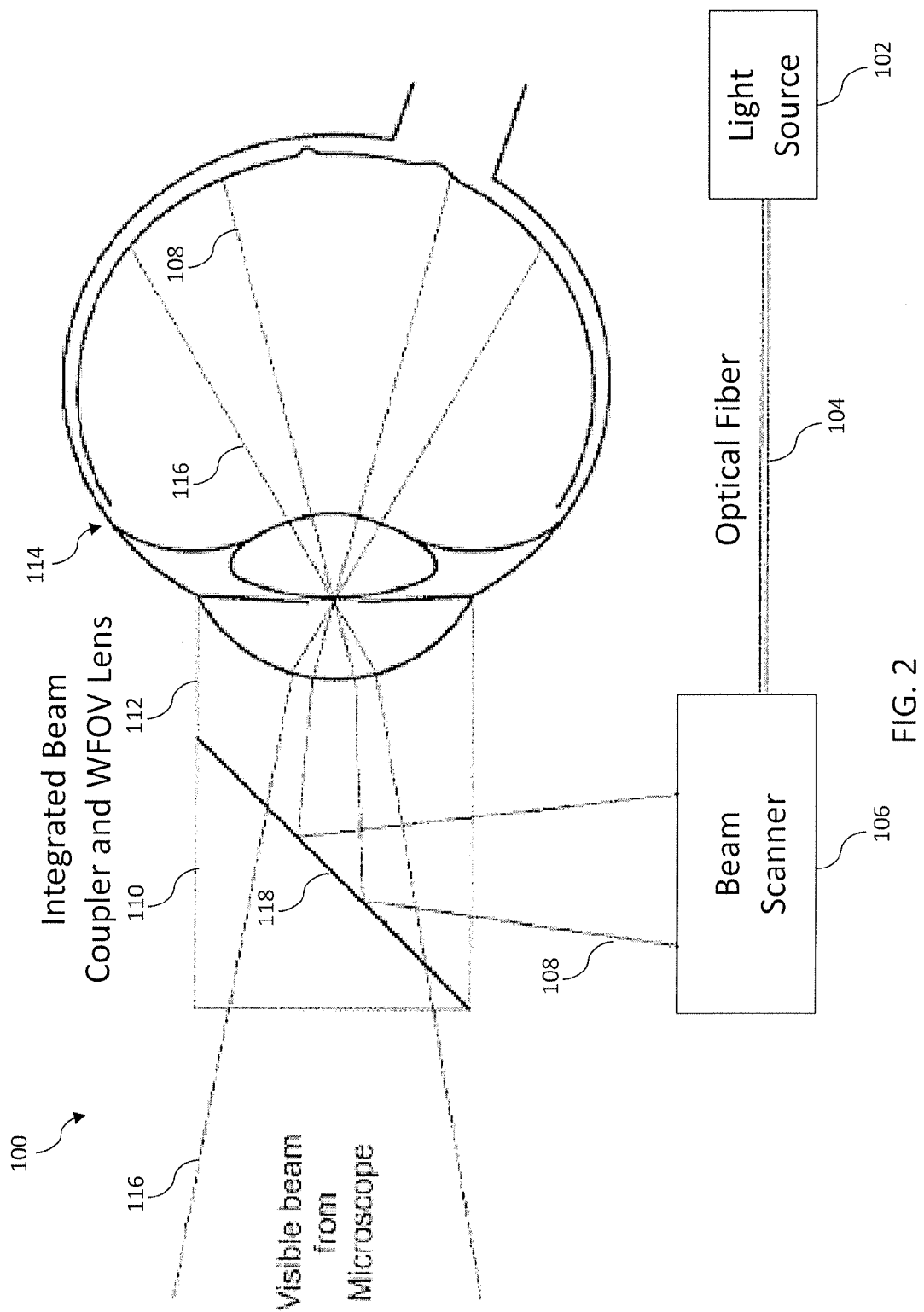
FIG. 2 is a diagram illustrating a microscope-less wide-field-of-view surgical OCT visualization system.
Figure 3:
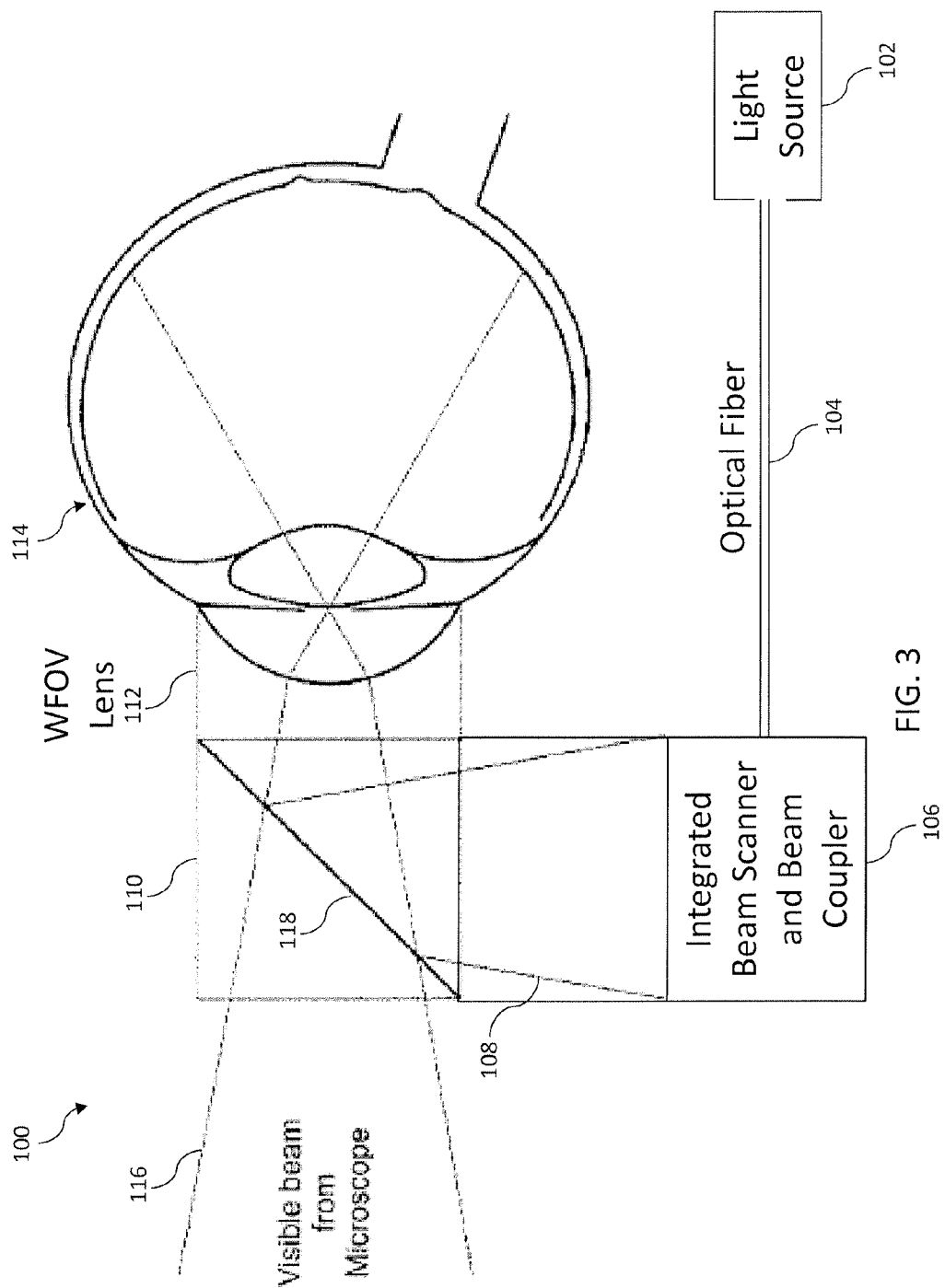
FIG. 3 is a diagram illustrating a microscope-less wide-field-of-view surgical OCT visualization system.
Figure 4:
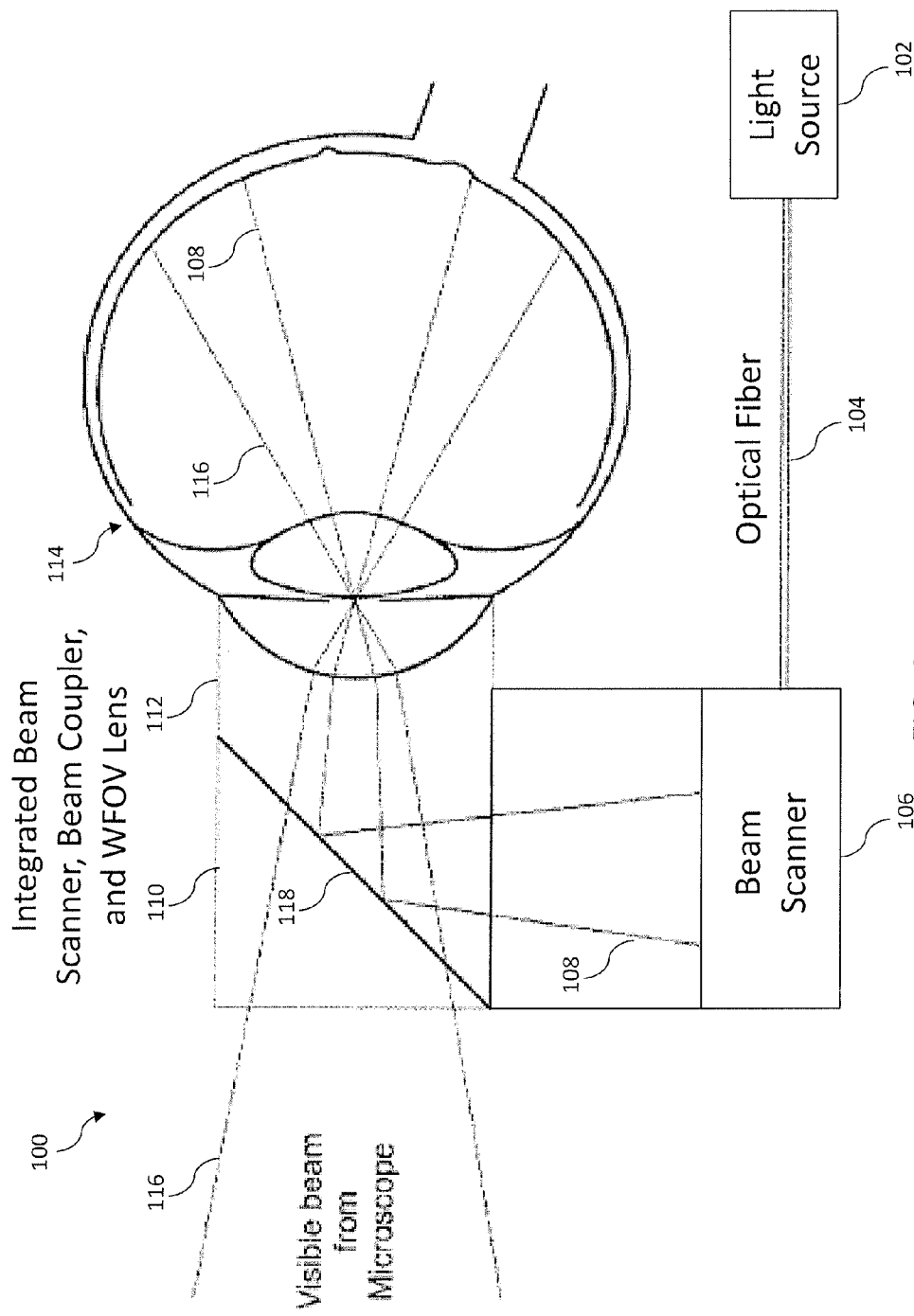
FIG. 4 is a diagram illustrating a microscope-less wide-field-of-view surgical OCT visualization system.
Figure 5:
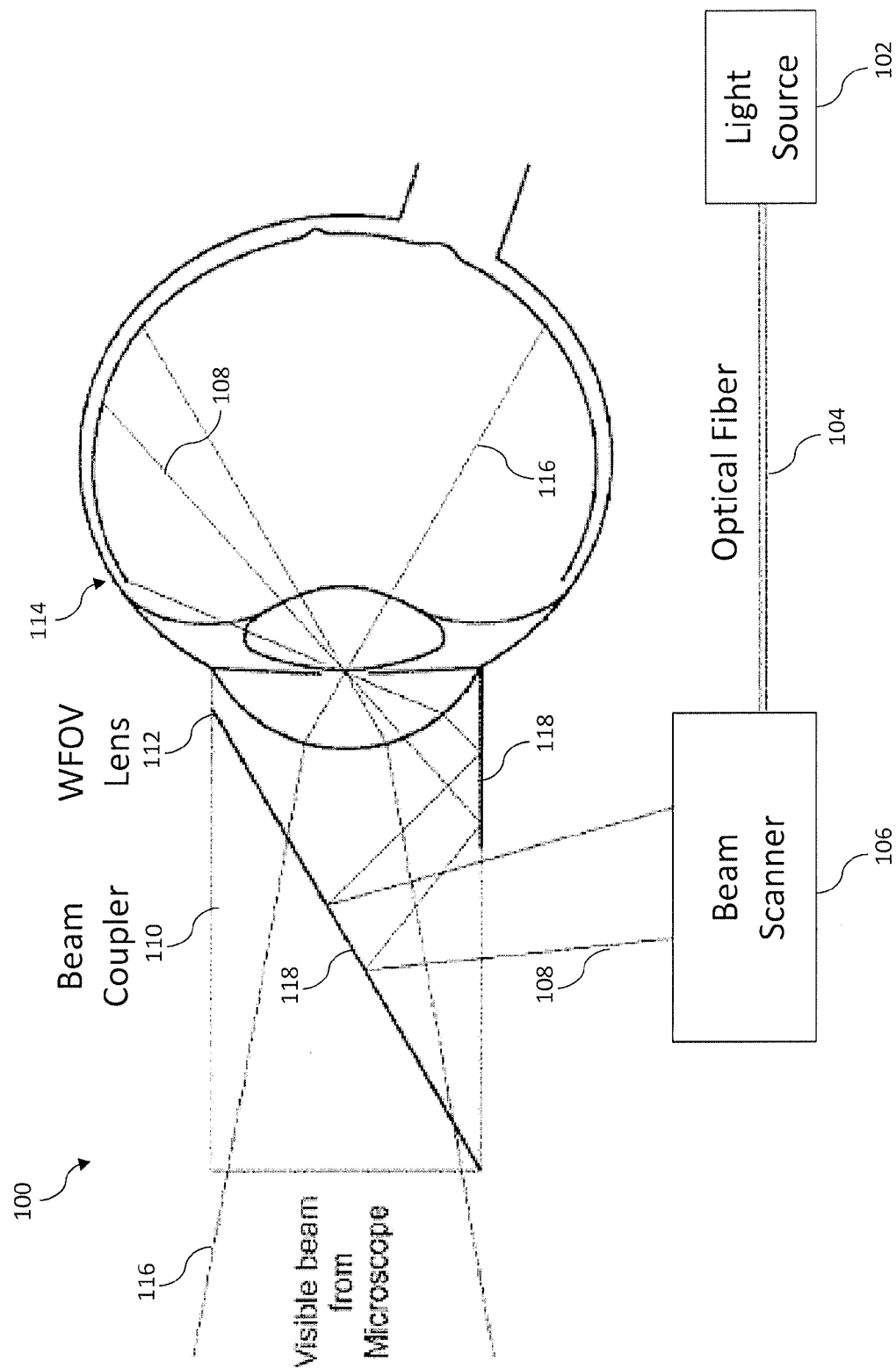
FIG. 5 is a diagram illustrating a microscope-less wide-field-of-view surgical OCT visualization system.
Figure 7:
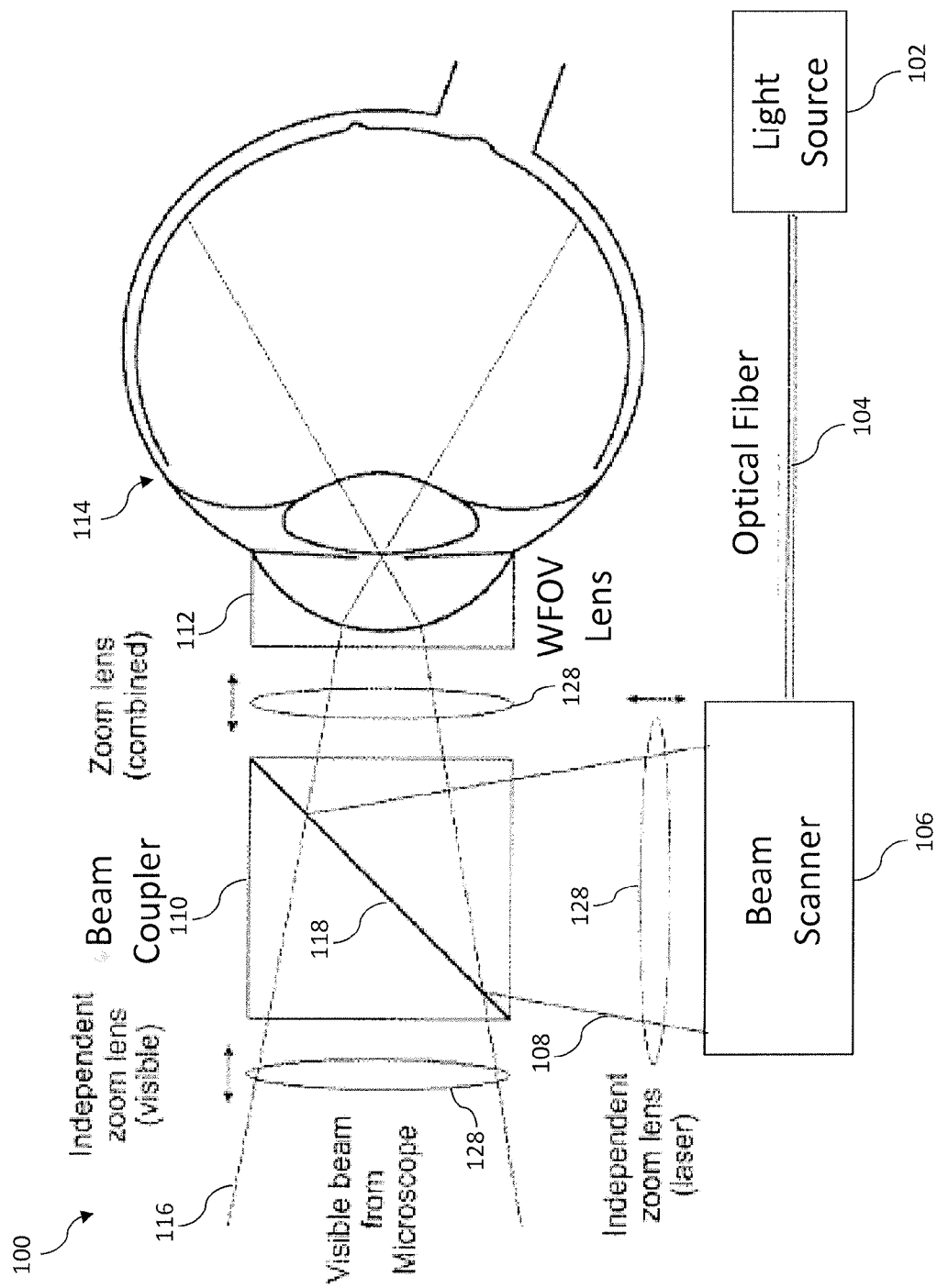
FIG. 7 is a diagram illustrating a microscope-less wide-field-of-view surgical OCT visualization system.

The surgical imaging system 100 can also include a surgical microscope. The beam coupler 110 can be configured to redirect the scanned imaging light beam 108 into an optical pathway 116 of the surgical microscope. To redirect the scanned imaging light beam 108 into the target region of the procedure eye 114 and/or the optical pathway 116 of the surgical microscope, the beam coupler 110 can include a mirror 118. As shown in FIG. 1, the mirror 118 can be tilted such that it is oriented at an oblique angle with respect to each of the scanned imaging light beam 108 and the optical pathway 116 of the surgical microscope. The mirror 118 can include a dichroic mirror, a notch filter, a hot mirror, a beamsplitter and/or a cold mirror. The mirror 118 can be configured to combine the visible beam of the microscope with the scanned imaging light beam 108. As a result, the field of view of the scanned imaging light beam 108 and the microscope can overlap completely (as shown in FIGS. 1, 3, and 7), overlap partially (as shown in FIGS. 2 and 4), or not overlap at all (as shown in FIG. 5).

The mirror 118 can be configured to reflect the scanned imaging light beam 108 and/or reflections from the procedure eye 114 in the wavelength range of the scanned imaging light beam 108 while allowing the visible beam of the microscope to pass therethrough. The mirror 118 can also be configured to reflect at least a portion of a visible guidance beam coincident with the scanned imaging light beam 108 to facilitate visualization of the scanned imaging light beam 108, which may be outside of the visible range, such as in the infrared range. For example, the mirror 118 can include a notch filter in the wavelength range of the visible guidance beam such that the visible guidance beam and its reflections from the procedure eye 114 can be reflected by the mirror 118 along with the scanned imaging light beam 108.

The beam coupler 110 can be operated with or without a defined optical/optomechanical relationship to the surgical microscope. For example, the beam coupler 110 can be maintained separate from and independently positionable relative to the surgical microscope. In such instances, the beam coupler 110 can be a hand-held device, a lens holder, a self-stabilized component or other component.

The beam coupler 110 and the WFOV lens 112 can be integrated into a common component such that the beam coupler 110 and the WFOV lens 112 can be collectively, independently positionable relative to the surgical microscope. FIG. 2 illustrates the surgical imaging system 100 having the beam coupler 110 and the WFOV lens 112 integrated into a common component, such as a hand-held device, a lens holder, an adapter, or other component. The WFOV lens 112 can be separate from, but attachable to the integrated optical block component. The integrated beam coupler 110 and WFOV lens 112 can be a consumable product configured for use in a single surgical procedure.

The beam scanner 106 and the beam coupler 110 can also be integrated into one optical block component. FIG. 3 illustrates the surgical imaging system 100 having the beam scanner 106 and the beam coupler 110 integrated into a common optical block component, such as a hand-held device, a lens holder, an adapter, or other component. The WFOV lens 112 can be separate from, but attachable to the integrated optical block component. The integrated beam scanner 106 and beam coupler 110 can be a consumable product configured for use in a single surgical procedure.

The beam scanner 106, the beam coupler 110, and the WFOV lens 112 can all be integrated into a common component. FIG. 4 illustrates the surgical imaging system 100 having the beam scanner 106, the beam coupler 110, and the WFOV lens 112 integrated into a common component, such as a hand-held device, a lens holder, an adapter, or other component. The integrated beam scanner 106, beam coupler 110, and WFOV lens 112 can be a consumable product configured for use in a single surgical procedure.

Referring again to FIG. 1, the beam coupler 110 can be coupled to the surgical microscope, directly or indirectly, such that it has a defined optical/optomechanical relationship to the surgical microscope. For example, the beam coupler 110 can be coupled to the surgical microscope by one or more of a suspension system, a mechanical frame, a protruding arm, a conical structure, a magnetic member, an elastic member, and a plastic member. The WFOV lens 112 can be independently manipulable relative to the procedure eye 114 by a lens-holder—instead of the beam coupler 110—when the beam coupler 110 is coupled to the surgical microscope in a defined optical/optomechanical relationship.

The WFOV lens 112 can be configured to provide a field of view of the procedure eye 114 greater than 15 degrees, greater than 30 degrees, greater than 45 degrees, greater than 60 degrees, greater than 80 degrees and/or greater than 100 degrees. Accordingly, the surgical imaging system 100 can be configured to provide various field of view ranges, such as between 0 degrees and 30 degrees, between 15 degrees and 80 degrees, between 30 degrees and 120 degrees, and/or other desired ranges up to ora serrata within the field of view of the WFOV lens 112. The WFOV lens 112 can be configured to provide the desired refractive power for the diagnostic and/or treatment procedures to be performed on the procedure eye 114.

The WFOV lens 112 can be configured to operate spaced from the procedure eye 114, as a non-contact lens, or in contact with the procedure eye 114, as a contact lens. For example, a non-contact WFOV lens 112 can be configured to operate in a manner similar to a binocular indirect ophthalmomicroscope (BIOM). The non-contact WFOV lens 112 can be positioned by one or more of a mechanical coupling to the beam coupler 110, a mechanical coupling to the surgical microscope, a suspension system, and a lens holder. The WFOV lens 112 can also be a contact lens configured to be contacted to the procedure eye 114. A contact WFOV lens 112 can be embedded in a stabilizing mechanism, where the stabilizing mechanism can be configured to stabilize the contact WFOV lens 112 relative to the procedure eye 114. To that end, the stabilizing mechanism can include one or more of a trocar, a counter weight, a friction-based system, and an elastic system.

The light source 102, the beam guidance system, and the beam scanner 106 can be part of an optical coherence tomographic (OCT) imaging system. To that end, the WFOV lens 112 and the beam coupler 110 can be configured to guide a returned image light from the target region of the procedure eye 114 back to the OCT imaging system. The returned image light can be interfered with a reference beam of the OCT imaging system, and from the interference an OCT image of the target region in a range of depths can be generated and displayed to a user. The surgical imaging system can be configured to generate the imaging information based on processing the returned image light in less than 30 seconds, less than 10 seconds, and/or less than 5 seconds, including in real time.

FIG. 5 illustrates the surgical imaging system 100 having a beam coupler 110 with a primary mirror 118 and an auxiliary mirror 118. The beam coupler 110 can also be integrated with the WFOV lens 112. The beam coupler 110 and the WFOV lens 112 can be configured to redirect the scanned imaging light beam 108 to angles larger than 15 degrees from an optical axis of the procedure eye 114. As shown in FIG. 5, the primary mirror 118 can be tilted such that it extends at an oblique angle with respect to each of the scanned imaging light beam 108 and the optical pathway 116 of the surgical microscope, while the secondary mirror 118 can be positioned such that it extends parallel (or close to parallel) to the optical pathway 116 of the surgical microscope and/or the optical axis of the procedure eye 114. As a result, the scanned imaging light beam 108 can be reflected from the primary mirror 118 to the secondary mirror 118 and through the WFOV lens 112 into the procedure eye 114. Each of the primary mirror 118 and the secondary mirror 118 can include a dichroic mirror, a notch filter, a hot mirror, a mirror, a reflector and/or a cold mirror. The primary mirror 118 and the secondary mirror 118 can have the same or different mirror type and/or features.

The primary mirror 118 and the second mirror 118 can have a fixed orientation such that the surgical imaging system 100 has a fixed, wide field of view. In that regard, the primary mirror 118 and the second mirror 118, along with the WFOV lens 112, can be configured to provide a field of view of the procedure eye 114 greater than 15 degrees, greater than 30 degrees, greater than 45 degrees, greater than 60 degrees, greater than 80 degrees and/or greater than 100 degrees. The primary mirror 118 and the second mirror 118 can be configured to scan in the periphery of the procedure eye 114. The primary mirror 118 and the second mirror 118 can also be configured to scan the trabecular meshwork or Schlemm's canal of the procedure eye 114. Further, the primary mirror 118 and the second mirror 118 can be configured such that the field of view of the scanned imaging beam 108 and the field of view of the visible beam of the microscope do not overlap, as shown in FIG. 5. The primary mirror 118 and the second mirror 118 can also be configured such that the field of view of the scanned imaging beam 108 and the field of view of the visible beam of the microscope partially or entirely overlap. The second mirror 118 can also be configured to be adjustable such that the field of view of the scanned imaging beam 108 is covering a changeable region of the procedure eye 114.

The beam coupler 110 can be rotatable relative to the procedure eye 114. In that regard, rotation of the beam coupler 110 can be utilized to facilitate full circumferential scanning of the procedure eye 114 and/or to target a particular region of interest within the procedure eye 114.

Rotation of the beam coupler 110 can be achieved manually (e.g., by physical manipulation by the surgeon) or automatically (e.g., by one or more motorized actuators controlled by a controller of the surgical imaging system 100). The WFOV lens can maintain a fixed orientation relative to the procedure eye 114 during rotation of the beam coupler 110.

One or both of the primary mirror 118 and the second mirror 118 can be movable to provide an adjustable field of view for the surgical imaging system 100. In that regard, in addition to providing a field of view greater than 15 degrees, greater than 30 degrees, greater than 45 degrees, greater than 60 degrees, greater than 80 degrees and/or greater than 100 degrees, the primary mirror 118 and the second mirror 118, along with the WFOV lens 112, can be configured to provide various field of view ranges, such as between 0 degrees and 30 degrees, between 15 degrees and 80 degrees, between 30 degrees and 120 degrees, and/or other desired ranges up to ora serrata within the field of view of the WFOV lens 112.

Figure 6:
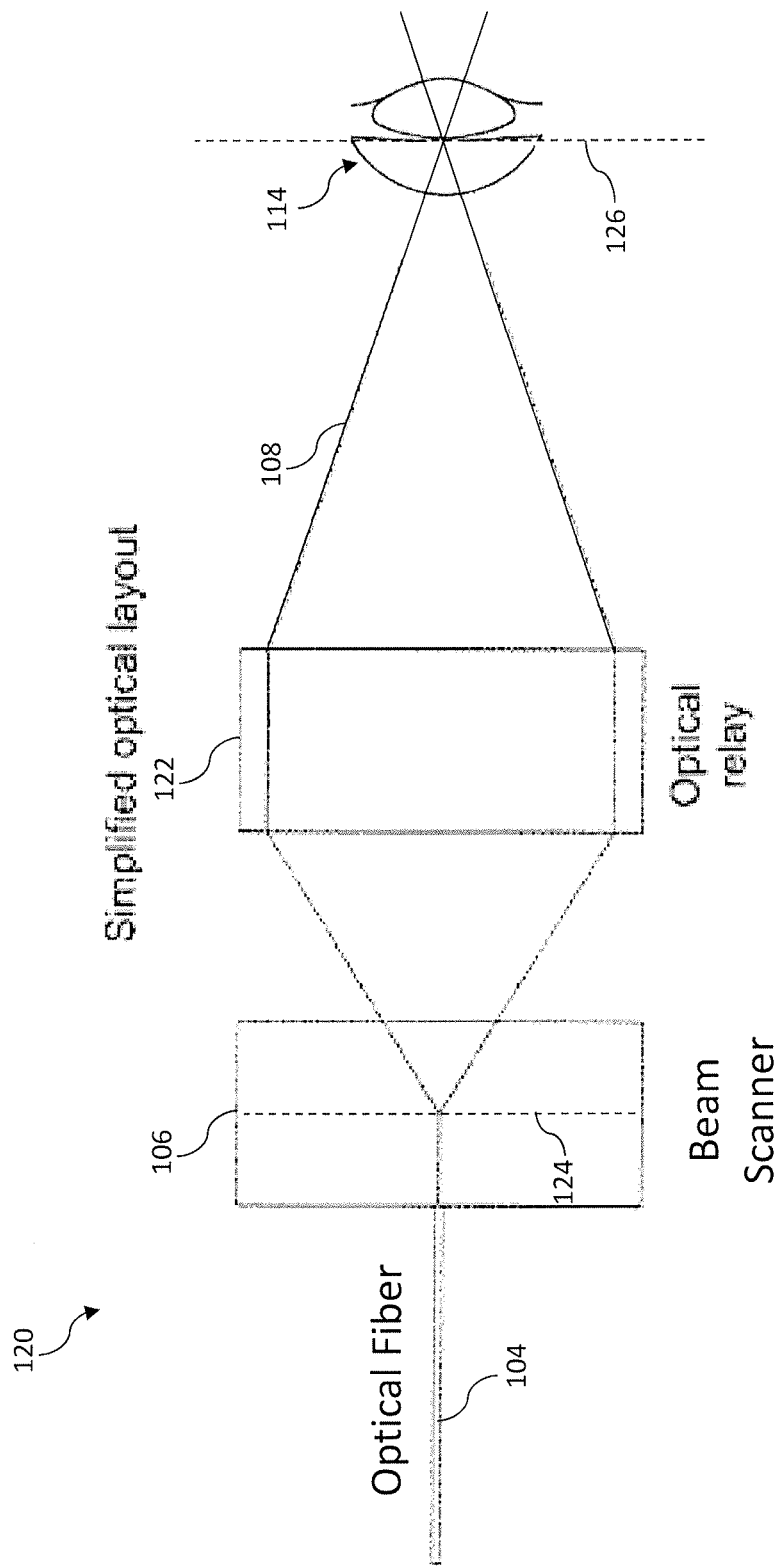
FIG. 6 is a diagram illustrating an optical layout of a microscope-less wide-field-of-view surgical OCT visualization system.

FIG. 6 illustrates an optical relay system 120 of the surgical imaging system 100. As shown, the optical relay system 120 can include an optical relay 122 configured to guide the scanned imaging light beam 108 to the procedure eye 114 so that the conjugate pupil plane 124 falls onto the beam scanner 106 and the scanned imaging light beam 108 pivots at a pupil plane 126 of the procedure eye 114. In that regard, the optical relay 122 can include any optical components (mirrors, lenses, filters, etc.) between the beam scanner 106 and the pupil plane 126 of the procedure eye 114, including optical components of the beam scanner 106, the beam coupler 110, the WFOV lens 112, the procedure eye 114, focusing optics, scanning optics, filtering optics, and/or other optical sub-systems. With the pupil plane 126 conjugate to the beam scanner 106, beam focusing can be used to optimize/adjust the focus of the scanned imaging beam 108 onto the retina or other regions of interest of the procedure eye 114.

FIG. 7 illustrates the surgical imaging system 100 having at least one adjustable zoom lens 128. The surgical imaging system 100 can include the adjustable zoom lens 128 at one or more of the following locations: between the beam coupler 110 and a surgical microscope; between the beam coupler 110 and the WFOV lens 112; between the beam coupler 110 and the beam scanner 106; and between the beam scanner 106 and the light source 102. An adjustable zoom lens 128 positioned between the beam coupler 110 and the surgical microscope can be configured to adjust the focus of the optical pathway 116 of the surgical microscope. An adjustable zoom lens 128 positioned between the beam coupler 110 and the beam scanner 106 or between the beam scanner 106 and the light source 102 can be configured to adjust the focus of the scanned imaging light beam 108. An adjustable zoom lens 128 positioned between the beam coupler 110 and the WFOV lens 112 can be configured to adjust the focus of both the optical pathway 116 of the surgical microscope and the scanned imaging light beam 108.

The adjustable zoom lens(es) 128 can be adjusted by a zoom-controller to adapt an optical power of the surgical imaging system to the desired target region of the procedure eye 114. Further, the adjustable zoom lens(es) 128 can be controlled by the zoom-controller in real-time to adapt the optical power of the surgical imaging system to keep an aberration below a predetermined value as the scanned imaging beam 108 scans across the target region of the procedure eye 114. In that regard, the zoom-controller can control each adjustable zoom lens 128 by adjusting a physical position of the zoom lens (e.g., using piezo-electric or other suitable actuators) and/or adjusting an optical power of the zoom lens without adjusting the physical position of the zoom lens (e.g., by varying a voltage supplied to a liquid crystal zoom lens).

Embodiments as described herein can provide devices, systems, and methods that facilitate real-time, intra-surgical, wide-field of view OCT imaging. The examples provided above are exemplary only and are not intended to be limiting. One skilled in the art may readily devise other systems consistent with the disclosed embodiments which are intended to be within the scope of this disclosure. As such, the application is limited only by the following claims.

The invention claimed is:

1. A surgical imaging system comprising:
   a light source, configured to generate an imaging light beam;
   a beam guidance system, configured to guide the imaging light beam from the light source;
   a beam scanner, configured
      to receive the imaging light from the beam guidance system, and
      to generate a scanned imaging light beam;
   a beam coupler, configured to redirect the scanned imaging light beam into an optical pathway of a surgical microscope, the optical pathway passing through the beam coupler; and
   a wide field of view (WFOV) lens integrated with the beam coupler, configured to contact a procedure eye and guide the redirected scanned imaging light beam into a target region of the procedure eye;
   wherein the integrated beam coupler and WFOV lens comprise a consumable product.

2. The surgical imaging system of claim 1, wherein:
   the surgical imaging system comprises the surgical microscope.

3. The surgical imaging system of claim 2, the beam coupler comprising at least one of:
   a dichroic mirror, a notch filter, a hot mirror, and a cold mirror in a tilted position.

4. The surgical imaging system of claim 2, wherein:
   the beam scanner and the beam coupler are integrated into one optical block.

5. The surgical imaging system of claim 1, wherein:
   the beam coupler is a hand-held device.

6. The surgical imaging system of claim 1, wherein:
   the WFOV lens is embedded in a stabilizing mechanism, the stabilizing mechanism configured to stabilize the WFOV lens relative to the procedure eye.

7. The surgical imaging system of claim 6, the stabilizing mechanism comprising at least one of:
   a trocar, a counter weight, a friction-based system, and an elastic system.

8. The surgical imaging system of claim 1, wherein:
   the WFOV lens has a field of view greater than 15 degrees.

9. The surgical imaging system of claim 1, wherein:
   the light source, the beam guidance system, and the beam scanner are part of an Optical Coherence Tomographic (OCT) imaging system; and
   the WFOV lens and the beam coupler are configured to guide a returned image light from the target region back to the OCT imaging system.

10. The surgical imaging system of claim 9, wherein:
    the surgical imaging system is configured to generate an imaging information based on processing the returned image light in less than 10 seconds.

11. The surgical imaging system of claim 1, wherein:
the beam scanner is at least one of
a micro-mirror device, a MEMS based device, a deformable platform, a galvanometer-based scanner, a polygon scanner and a resonant PZT scanner.

12. The surgical imaging system of claim 1, wherein:
the light source has an operating wavelength in the 0.2-1.8 micron wavelength range.

13. The surgical imaging system of claim 1, wherein:
the beam coupler comprises a primary mirror and an auxiliary mirror, configured to redirect the light beam to angles larger than 15 degrees from an optical axis of the procedure eye.

14. The surgical imaging system of claim 13, wherein:
at least one of the primary mirror and the auxiliary mirror is movable to provide an adjustable field of view.

15. The surgical imaging system of claim 13, wherein:
the beam coupler is rotatable.

16. The surgical imaging system of claim 1, comprising:
an optical relay system, configured to guide the scanned imaging light beam to the procedure eye so that the conjugate pupil plane falls onto the beam scanner and the imaging light pivots at the pupil plane.

17. The surgical imaging system of claim 1, comprising at least one of:
an adjustable zoom lens between the beam coupler and a surgical microscope;
an adjustable zoom lens between the beam coupler and the WFOV lens;
an adjustable zoom lens between the beam coupler and the beam scanner; and
an adjustable zoom lens between the beam scanner and the light source.

18. The surgical imaging system of claim 17, wherein:
an adjustable zoom lens is movable by a zoom-controller to adapt an optical power of the surgical imaging system to keep an aberration below a predetermined value as the scanned imaging beam is scanned in the target region.

19. The surgical imaging system of claim 1, the beam guidance system comprising at least one of:
a fiber optical guide and a free space guidance system.

20. An apparatus for use in a surgical imaging system, the apparatus comprising:
a beam coupler, configured to redirect a scanned imaging light beam into an optical pathway of a surgical microscope, the optical pathway passing through the beam coupler; and
a wide field of view (WFOV) lens integrated with the beam coupler, configured to contact a procedure eye and guide the redirected scanned imaging light beam into a target region of the procedure eye;
wherein the integrated beam coupler and WFOV lens comprise a consumable product.

21. The apparatus of claim 20, further comprising:
a beam scanner, configured to
receive an imaging light from a beam guidance system, and
generate the scanned imaging light beam.

* * * * *